US00PP14278P29

(12) United States Plant Patent
Hanes

(10) Patent No.: US PP14,278 P2
(45) Date of Patent: Nov. 4, 2003

(54) PETUNIA PLANT NAMED 'WHIP ROSE'

(50) Latin Name: *Petunia hybrida*
Varietal Denomination: Whip Rose

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/389,056
(22) Filed: Mar. 13, 2003
(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates, PC

(57) ABSTRACT

A petunia cultivar particularly distinguished by rose colored flowers, compact habit and good basal branching.

1 Drawing Sheet

Genus and species: *Petunia hybrida.*
Variety denomination: 'Whip Rose'.

BACKGROUND OF THE NEW PLANT

The present invention comprises a new and distinct cultivar of petunia, botanically known as *Petunia hybrida,* and hereinafter referred to by the cultivar name 'Whip Rose'. The new cultivar is asexually reproduced from vegetative cuttings and tissue culture resulting from the cross of the seed/pod parent 99-189-1, a red proprietary line that is unnamed and unpatented ×99-1-4, a purple proprietary line that is unnamed and unpatented.

'Whip Rose' is a product of a planned breeding program intended to create new petunia plants with a rose colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers

DESCRIPTION OF THE NEW CULTIVAR

The following detailed descriptions set forth the distinctive characteristics of 'Whip Rose'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms: Approximately 10–15 cm.
Width: Approximately 50–60 cm including flowers.
Time to produce a finished flowering plant: 9–11 weeks.
Outdoor plant performance: Full sun, free- flowering through the summer, some heat tolerance. Use in hanging baskets, mixed containers, and mass plantings.
Time to initiate roots: Approximately 18–24 days in the greenhouse.
Root description: Fibrous, white.

THE LEAVES

Arrangement: Alternate, upper leaves sub-opposite.
Length: 4.0–4.3 cm.
Width: 2.7–2.9 cm.
Leaf blade shape: Ovate.
Leaf margin: Entire.
Apex aspect: Acute/Rounded.
Base aspect: Acuminate.
Leaf color: Upper side: RHS 137A (green) but a little darker. Underside: RHS 137C (green).
Texture: Sparse glandular hairs.
Venation: Palmate.
Venation color: RHS 144A (yellow-green).
Petiole length: 0.3–0.5 cm.
Petiole width: 0.25–0.3 cm.
Petiole color: RHS 144A (yellow-green).
Petiole texture: Sparse glandular hairs.

THE STEM

Length: 40–50 cm.
Diameter: 0.3 cm.

Internode length: 0.5–2.5 cm.
Color: RHS 143C (green) and RHS 144A (yellow-green).
Texture: Sparse glandular hairs.
Stem anthocyanin: No.
Peduncle color: RHS 143C (green).
Peduncle length: 2.0–3.7 cm.
Peduncle diameter: 0.1 cm.
Peduncle texture: Many glandular hairs of various sizes.

THE BUD

Shape: Oblong.
Diameter: 0.3–0.5 cm.
Length: 2.0–3.5 cm.
Color at tight bud: RHS 182B (greyed-red).

THE FLOWER

Blooming habit: Continuous all through the growing season. Good floriferousness.
Inflorescence type: Flowers solitary in upper leaf axis.
Young flower color: RHS 67A (red-purple) base color; RHS 187A (greyed-purple) mid-veins; RHS 60A (red-purple) heavy secondary veining, with heavy amount of red tones bleeding into the petals.
Young flower floret diameter: 3.3–3.6 cm.
Mature flower color: Front side, RHS 67A (red-purple) base color; RHS 187A (greyed-purple) mid-veins; lighter intensity but heavy in quantity RHS 60A (red-purple) secondary veins, with some red tones bleeding into the petals.
Mature flower color: Underside, lighter hue of RHS 75A (purple) extending out to the margins on both sides of the mid-veins, and between RHS 68A/B (red-purple) mostly of a wide band at the margin between the mid-veins; Heavy front side veining showing through.
Corolla tube color inside: RHS 159A (orange-white) base color; RHS 187A (greyed-purple) mid-veins; RHS 183A (greyed-purple) heavy secondary veining.
Corolla tube length: 2.2–2.5 cm.
Corolla outside texture: Many glandular hairs.
Floret form and number of petals: Funnel form, 5 lobed petals fused at base; calyx, 5 deeply lobed.
Flower (limb) diameter: 3.9–4.2 cm.
Petal apex shape: Acute.
Petal base shape: Fused.
Petal margin: Entire.
Petal lobation: Moderate.
Petal waviness: Moderate.
Petal texture: Papillose.
Sepal color: RHS 137A (green).
Sepal length: 1.0–1.2 cm.
Sepal width: 0.2–0.3 cm.
Sepal shape: Oblong.
Sepal apex: Obtuse.
Sepal texture: Many glandular hairs of various sizes.
Lastingness of individual blooms: 4–8 days.
Fragrance: Slightly sweet.

THE REPRODUCTIVE ORGANS

Stamens: Five, 2 taller and 3 shorter.
Filament color: RHS 145D (yellow-green).
Pollen color: RHS 11C (yellow).
Pistil: One.
Stigma: RHS 145 C (yellow-green) at the edges and RHS 144A (yellow-green) in the center.
Style color: RHS 145C (yellow-green).
Fruit seed set: Not observed.

DISEASE AND INSECT RESISTANCE

Not observed.

COMPARISON WITH PARENTAL CULTIVARS

Compares to its female parent 99-189-1 in the following ways: The female parent is an upright growing, late flowering, and red flower plant with medium size flowers. 'Whip Rose' is an earlier flowering moderately vigorous plant with rose-colored flowers.

Compares to its male parent 99-1-4 in the following ways: The male parent is a late flowering, trailing plant with purple flowers. 'Whip Rose' is an earlier flowering, more free flowering plant with rose flowers that does not trail as much as the male parent.

I claim:

1. A new and distinct petunia plant as shown and described herein.

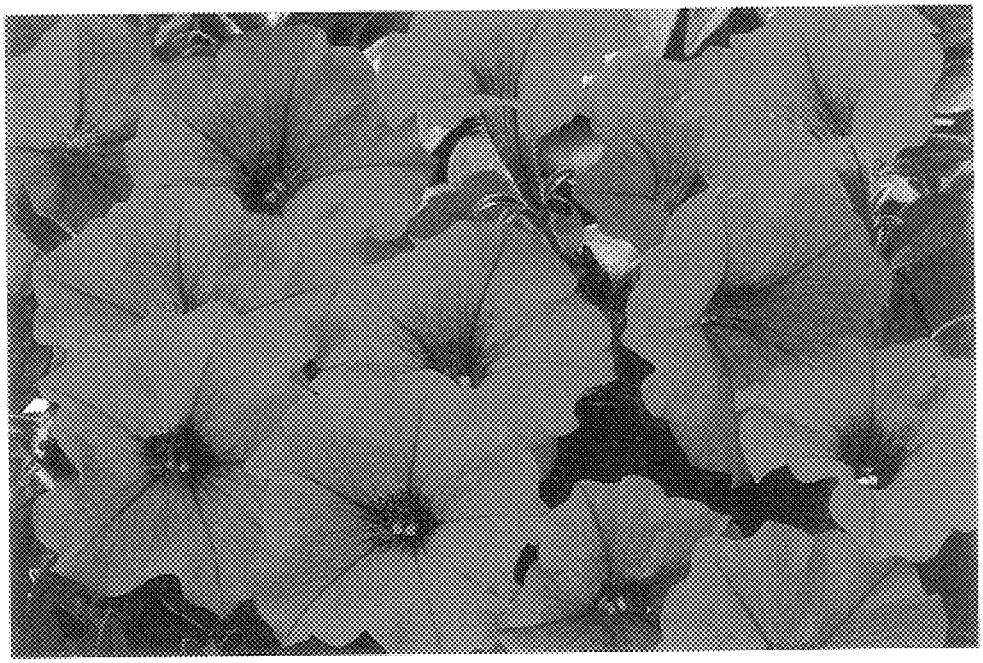

* * * * *